United States Patent
Shirai et al.

[11] Patent Number: 5,990,463
[45] Date of Patent: Nov. 23, 1999

[54] OXYGEN SENSOR ELEMENT HOLDING LAMINATION TYPE CERAMIC HEATER

[75] Inventors: Makoto Shirai; Masayuki Kobayashi, both of Kuwana, Japan

[73] Assignee: Denso Corporation, Kariya, Japan

[21] Appl. No.: 09/090,980

[22] Filed: Jun. 5, 1998

[30] Foreign Application Priority Data

Jun. 13, 1997 [JP] Japan ................. 9-173020
May 11, 1998 [JP] Japan ................. 10-127913

[51] Int. Cl.$^6$ ........................... H05B 3/44
[52] U.S. Cl. ................. 219/544; 219/542; 219/543
[58] Field of Search ................. 219/544, 542, 219/209; 338/243; 204/424, 425, 426, 427, 242; 73/31.05

[56] References Cited

U.S. PATENT DOCUMENTS

| | | | |
|---|---|---|---|
| 4,578,174 | 3/1986 | Kato et al. | 204/429 |
| 4,636,293 | 1/1987 | Bayha et al. | |
| 4,824,550 | 4/1989 | Ker et al. | 204/427 |
| 5,098,548 | 3/1992 | Duce | 204/424 |
| 5,139,639 | 8/1992 | Holleboom | 204/427 |
| 5,271,821 | 12/1993 | Ogasawara et al. | 204/429 |
| 5,393,397 | 2/1995 | Fukaya et al. | 204/424 |
| 5,451,748 | 9/1995 | Matsuzaki et al. | |
| 5,685,964 | 11/1997 | Watanabe et al. | 204/429 |
| 5,759,365 | 6/1998 | Yamada et al. | 204/424 |

FOREIGN PATENT DOCUMENTS

| | | |
|---|---|---|
| 42 32 092 A1 | 3/1994 | Germany. |
| 197 02 096 A1 | 7/1997 | Germany. |
| 4-157358 | 5/1992 | Japan. |
| 9-203718 | 8/1997 | Japan. |
| 94/14057 | 6/1994 | WIPO. |

OTHER PUBLICATIONS

JP 04 157358 A (Nippondenso Co. Ltd.), May 29, 1992 & Database WPI Section Ch, Week 9225, Derwent Publications Ltd., London, GB, Class E36, AN 92–231513, XP002078850 & Patent Abstracts of Japan, vol. 16, No. 448 (P–1432–), Sep. 17, 1992.

JP 05 126789 A (Hitachi Ltd.), May 21, 1993 & Patent Abstracts of Japan, vol. 17, No. 495 (P–1608), Sep. 7, 1993, XP002078849.

*Primary Examiner*—Teresa Walberg
*Assistant Examiner*—Vinod D Patel
*Attorney, Agent, or Firm*—Nixon & Vanderhye P. C.

[57] ABSTRACT

An oxygen sensor element has a cup-type solid electrolyte body defining an air chamber therein, and a plate-like lamination-type ceramic heater is disposed in the air chamber with a front end portion contacting the bottom portion of the air chamber. Accordingly, the lamination type ceramic heater is prevented form being swung and hit against the electrolyte body.

18 Claims, 11 Drawing Sheets

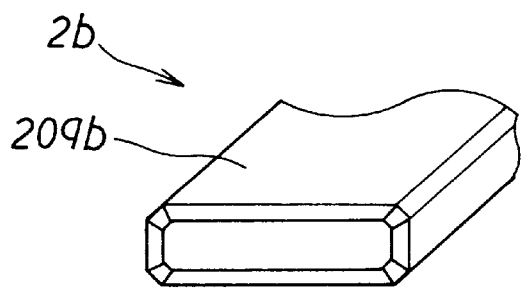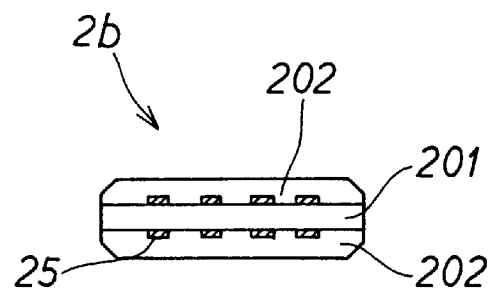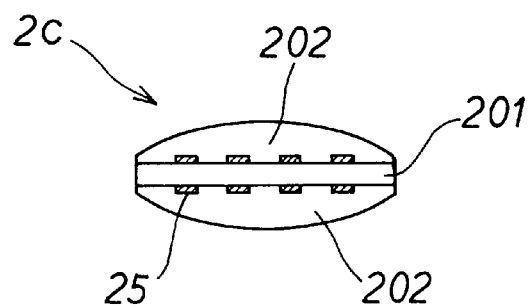

(COMPARATIVE SAMPLE C1)

(SAMPLE 1)

(SAMPLE 2)

(SAMPLE 3)

(SAMPLE 4)

OXYGEN SENSOR ELEMENT HOLDING LAMINATION TYPE CERAMIC HEATER

CROSS REFERENCE TO RELATED APPLICATIONS

This application is based upon and claims the benefit of priority of prior Japanese Patent Applications No. 9-173020 filed on Jun. 13, 1997, and No. 10-127913 filed on May 11, 1998, the contents of which are incorporated herein by reference.

BACKGROUND OF THE INVENTION

1. Field of the Invention

The present invention relates to an oxygen sensor element that holds a lamination type ceramic heater, which is applied to an exhaust system of an internal combustion engine to control an air fuel ratio of the engine.

2. Related Art

Conventionally, an air fuel ratio sensor is installed in an exhaust system of an automotive engine to detect an air fuel ratio, and the combustion of the engine is controlled based on the detected air fuel ratio. An oxygen sensor containing an oxygen sensor element is widely employed as the air fuel ratio sensor.

The oxygen sensor element is composed of a cup-like solid electrolyte body having oxygen ion conductivity and defining an air chamber therein, an outer electrode disposed on an outer surface of the solid electrolyte body, and an inner electrode disposed on an inner surface of the solid electrolyte body. The inner surface of the solid electrolyte body is exposed to the air chamber. Further, a ceramic heater is disposed in the air chamber to heat the oxygen sensor element to an activation temperature. A pole-like ceramic heater is typically employed as the ceramic heater.

In recent years, to reduce manufacturing cost, a plate-like lamination type ceramic heater has been suggested as a replacement for the pole-like ceramic heater. For example, JP-A-7-35723, JP-B2-5-2101, and WO 94/14057 disclose this kind of ceramic heater. The lamination type ceramic heater is composed of a plurality of laminated heater substrates, one of which has a heater layer for developing heat, and a lead layer for supplying electricity to the heater layer.

However, the mechanical strength of the lamination type ceramic heater is smaller than that of the pole-like ceramic heater. As mentioned above, the ceramic heater is disposed within the air chamber of the oxygen sensor element. Within the air chamber, the ceramic heater may be swung like a pendulum into contact with the solid electrolyte body due to impact, vibrations, and the like applied externally to the oxygen sensor element. In such a case, the lamination type ceramic heater is easily damaged. The damage to the ceramic heater can involve not only the heater substrates but the heater and lead layers to cause electrical disconnection. In addition, the heater and lead layers can be oxidized by air coming through the damaged portion, resulting in an increase in resistance of the heater and lead layers.

SUMMARY OF THE INVENTION

The present invention has been made in view of the above-mentioned problems. An object of the present invention is to provide an oxygen sensor element securely holding a lamination type ceramic heater therein. Another object of the present invention is to prevent damage to a lamination type ceramic heater installed in an air chamber of an oxygen sensor element.

Briefly, an oxygen sensor element according to the present invention has a solid electrolyte body defining an air chamber therein and a plate-like lamination type ceramic heater disposed in the air chamber. The lamination ceramic heater has an end portion contacting an inner surface of the electrolyte body at a bottom portion of the air chamber. Accordingly, the lamination type ceramic heater is prevented from being swung against the solid electrolyte body. Consequently, the ceramic heater is prevented from being damaged. In addition, because the ceramic heater contacts the solid electrolyte body, heat transfer efficiency from the ceramic heater to the solid electrolyte body is improved.

Preferably, the end portion of the ceramic heater has two faces with radiuses of curvature different from one another. More preferably, the end portion of the ceramic heater has a tapered face contacting the inner surface of the electrolyte body, and a top face on the top portion of the end portion. Accordingly, the ceramic heater contacts the inner surface of the electrolyte body at the bottom portion of the air chamber.

The top face may be flat. In this case, the ceramic heater can be manufactured by tapering an end portion of a plate-like lamination body to retain the top flat face. The tapered face of the end portion may be a curved face or a plurality of flat faces. The top face can have a radius of curvature larger than that of the bottom portion of the air chamber. The tapered face can have a portion with a radius of curvature smaller than that of the bottom portion of the air chamber.

BRIEF DESCRIPTION OF THE DRAWINGS

These and other objects and features of the present invention will become more readily apparent from a better understanding of preferred embodiments described below with reference to the following drawings.

FIG. 6A is a perspective view showing a front end portion of a ceramic heater in a third embodiment;

FIG. 6B is a cross-sectional view showing the ceramic heater in the third embodiment;

FIG. 7 is a cross-sectional view showing a ceramic heater in a fourth embodiment;

DETAILED DESCRIPTION OF THE PREFERRED EMBODIMENTS (First Embodiment)

Figure 1:
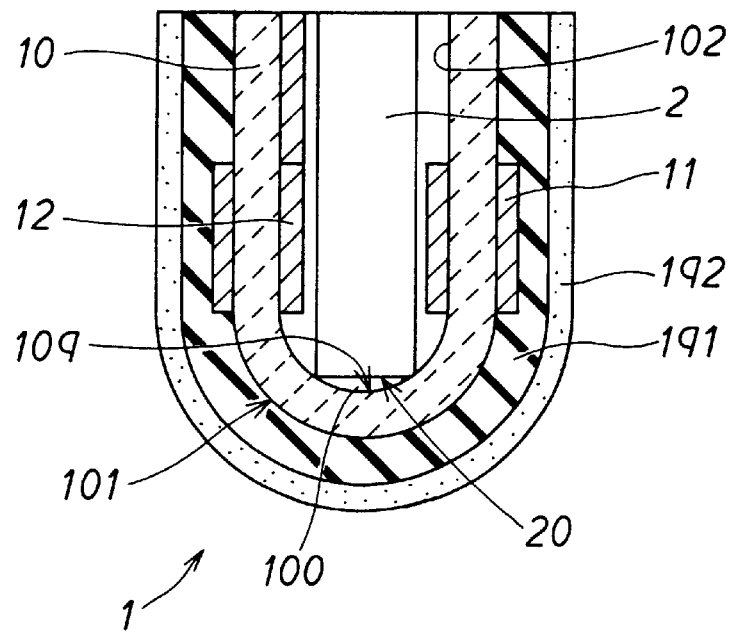
FIG. 1 is a cross-sectional view partially showing an oxygen sensor element holding a ceramic heater therein in a first embodiment.

An oxygen sensor element 1 in a first preferred embodiment will be explained with reference to FIGS. 1–3. As shown in FIG. 1, the oxygen sensor element 1 is composed of a cup-type solid electrolyte body 10 having an air chamber 100 therein, an outer electrode 11 provided on an outer surface 101 of the solid electrolyte body 10, and an inner electrode 12 provided on an inner surface 102 of the solid electrolyte body 10. The inner surface 102 of the solid electrolyte body 10 is exposed to the air chamber 100. The outer surface 101 of the solid electrolyte body 10 is covered with a protection layer 191 with the outer electrode 11 interposed therebetween, and the protection layer 191 is further covered with a trap layer 192.

A plate-like lamination type ceramic heater 2 is held within the air chamber 100. The bottom portion 109 of the air chamber 100 has an arc-like concave shape relative to the ceramic heater 2, and a front end face 20 of the ceramic heater 2 having a rectangular shape abuts the bottom portion 109 of the air chamber 100 at four corner points thereof.

Figure 2:
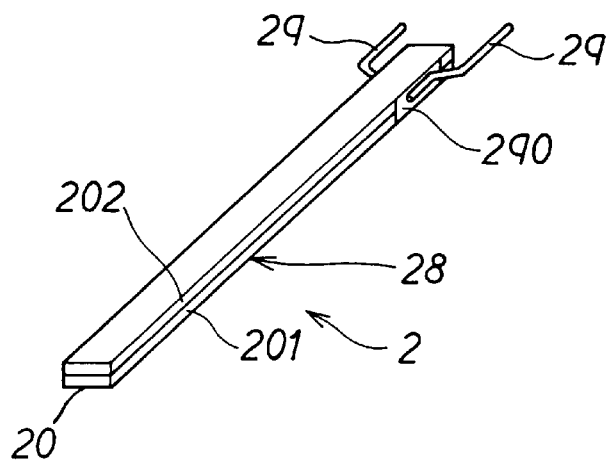
FIG. 2 is a perspective view showing the ceramic heater in the first embodiment.

As shown in FIG. 2, the ceramic heater 2 is composed of a heater substrate 201 holding a heater layer for developing heat, a lead layer for supplying electricity to the heater layer thereon, and a cover substrate 202 disposed on the heater substrate 201 to cover the heater layer and the lead layer. The heater substrate 201 and the cover substrate 202 are made of alumina ($Al_2O_3$). The heater and lead layers are made of a conductive material containing tungsten (W). Parts of the lead layer are exposed on both side surfaces 28 of the ceramic heater 2, and conductive members 290 are disposed on the exposed lead layer on the side surfaces 28. Further, lead wires 29 are connected to the conductive members 290.

Figure 3:
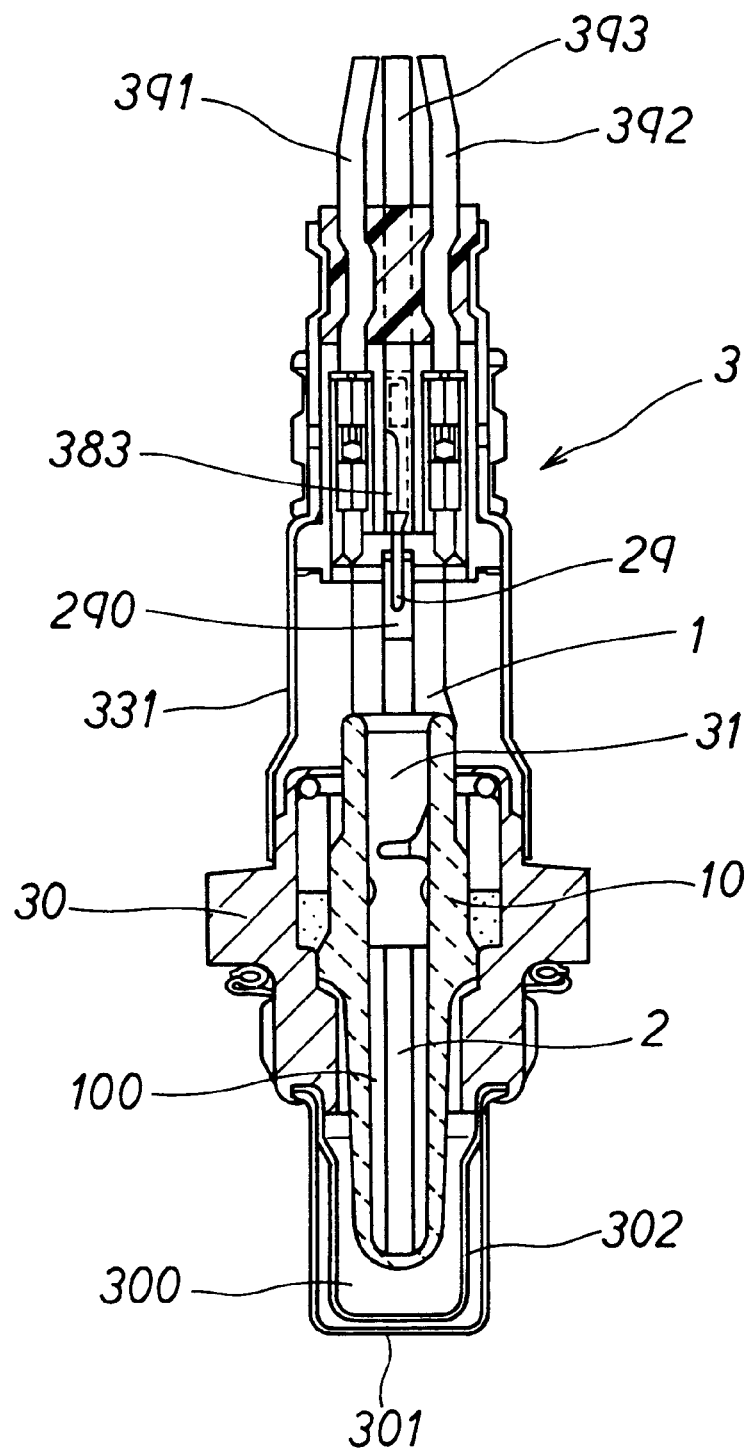
FIG. 3 is a cross-sectional view showing an oxygen sensor in the first embodiment.

The above-mentioned oxygen sensor element 1 is disposed in an oxygen sensor 3 as shown in FIG. 3. The oxygen sensor 3 is composed of a housing 30 for holding the oxygen sensor element 1, measurement gas side covers 301, 302 covering the lower portion of the housing 30 and defining a measurement gas chamber 300 therein, and an air side cover 331 covering the upper portion of the housing 30. A heater holder 31 is inserted into the air chamber 100 of the oxygen sensor element 1 so that the ceramic heater 2 is fixed to the oxygen sensor element 1 within the air chamber 100. The inner and outer electrodes 11, 12 of the oxygen sensor element 1 are connected to lead wires 391, 392 for taking out an output signal from the oxygen sensor element 1. The lead wires 29 of the ceramic heater 2 are connected to lead wires 393 for supplying electricity to the ceramic heater 2, through terminals 383.

Next, features and effects in the first embodiment will be explained. In the oxygen sensor element 1, the ceramic heater 2 abuts the bottom portion 109 of the air chamber 100 at four points. When the oxygen sensor element 1 is installed in the oxygen sensor 3, the upper portion of the ceramic heater 2 is supported by the heater holder 31, while the lower portion of the ceramic heater 2 is supported by the bottom portion 109 of the air chamber 100 at the four points. As a result, the ceramic heater 2 is securely fixed to the solid electrolyte body 10 of the oxygen sensor element 1 within the air chamber 100 and does not swing and vibrate within the air chamber 100, thereby preventing damage to the ceramic heater 2.

(Second Embodiment)

Figure 4A:
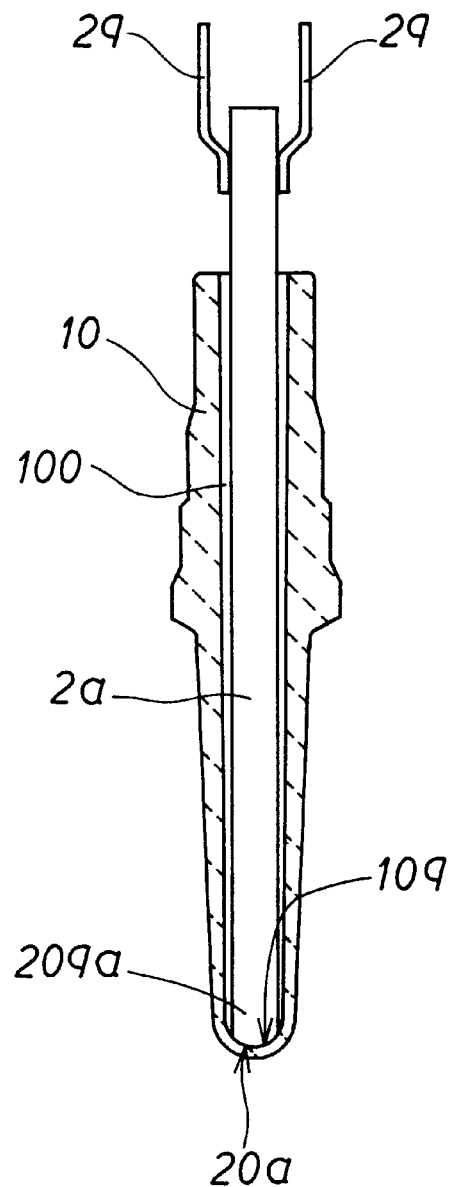
FIG. 4A is a cross-sectional view showing the oxygen sensor element and a ceramic heater installed in the oxygen sensor, taken from a front face side of the ceramic heater in a second embodiment.
Figure 4B:
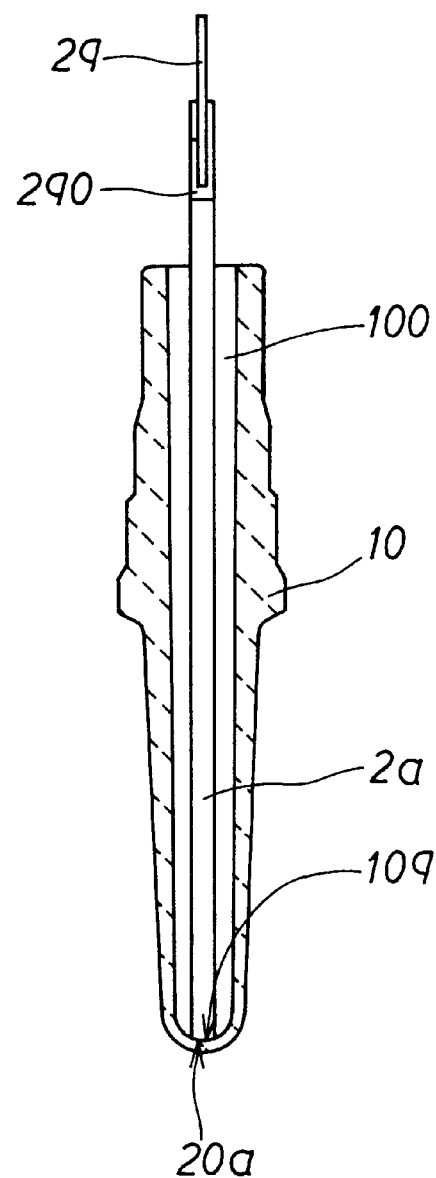
FIG. 4B is a cross-sectional view showing the oxygen sensor element and the ceramic heater of FIG. 4A, taken from a side face side of the ceramic heater.

In a second preferred embodiment, as shown in FIGS. 4A, 4B, a ceramic heater 2a has a front end portion 209a with a front end curved face 20a. The radius of curvature of the front end curved face 20a is approximately the same as that of the bottom portion 109 of the air chamber 100 so that the front end face 20a contacts the entire bottom portion 109. The other features are the same as those in the first embodiment. In the second and the successive embodiments, the same parts and components as those in the first embodiment are indicated with the same reference numerals and the same descriptions will not be reiterated.

Next, a method of manufacturing the ceramic heater 2a will be explained. First, slurry is formed from source powders composed of 92 wt % $Al_2O_3$ and 8 wt % mixture of silicon dioxide ($SiO_2$) and magnesium oxide (MgO). The slurry is formed into a sheet with 1.2 mm in thickness by a doctor blade method. Then, two square green sheets 41, 42 sized to 120 mm×120 mm are stamped out from the sheet by a punching press method. The green sheet 41 is for the heater substrate 201 and the green sheet 42 is for the cover substrate 202. The green sheets 41, 42 can be formed by other methods, such as an extrusion method.

Figure 5A:
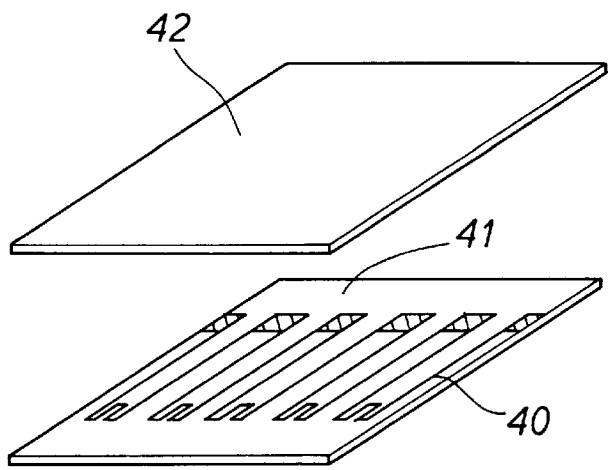
FIGS. 5A–5E are schematic views for explaining a method of manufacturing the ceramic heater in the second embodiment.
Figure 5B:
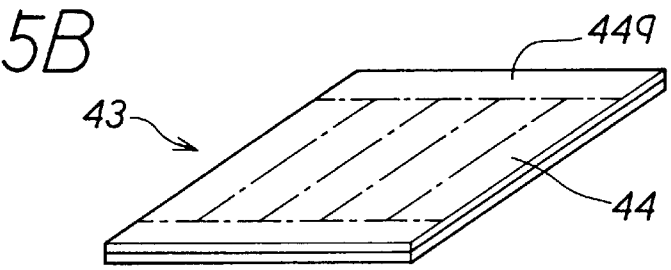

Next, conductive paste containing metallic materials such as W and molybdenum (Mo) is printed on the green sheet 41 for the heater substrate 201 to form five heater patterns 40 for the heat and lead layers as shown in FIG. 5A. Then, the green sheet 42 is laminated with the green sheet 41 such that the heater patterns 40 are interposed between the green sheets 41, 42, thereby forming a lamination body 43 as shown in FIG. 5B. The lamination body 43 is dried.

Figure 5C:
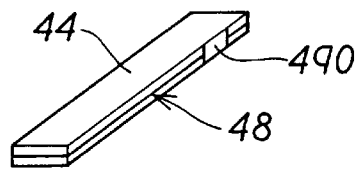

After it is dried, the lamination body 43 is cut along dashed lines shown in FIG. 5B so that it is divided into five intermediate bodies 44 holding a corresponding one of the heater patterns 40. At that time, edge portions 449 including no heater pattern therein are removed. One of the intermediate bodies 44 is shown in FIG. 5C. Herebelow, descriptions will be done with respect to the one intermediate body 44. Successively, conductive paste is printed on side surfaces 48 of the intermediate body 44 where parts of the heater pattern 40 are exposed, thereby forming printed portions 490. Then, the intermediate body 44 is baked at a temperature in a range of 1400° C.–1600° C. The baked intermediate body is indicated with reference numeral 45 in FIG. 5D. Simultaneously, the printed portions 490 are baked to serve as the conductive members 290.

Figure 5D:
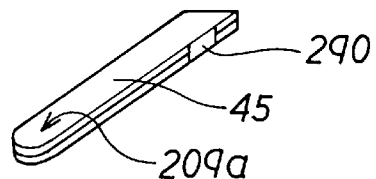
Figure 5E:
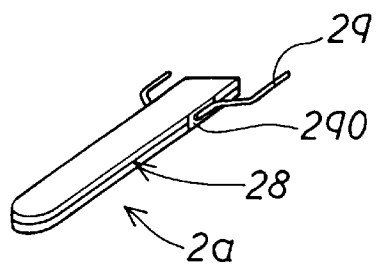

Next, the front end portion 209a of the baked intermediate body 45 is polished by a polishing machine to have the same radius of curvature as that of the bottom portion 109 of the air chamber 100 as shown in FIG. 5D. After brazing filler metal containing copper (Cu) and the like is disposed on the conductive members 290, the lead wires 29 are brazed to the conductive members 290 through the brazing filler metal at 1100° C.–1150° C. within a furnace. As a result, the ceramic heater 2a shown in FIG. 5E is provided.

In the second embodiment, the ceramic heater 2a can be more stably disposed within the air chamber 100 of the oxygen sensor element 1. In addition, because the front end face 20a of the ceramic heater 2a contacts the entire bottom portion 109 of the air chamber 100, heating efficiency of the ceramic heater 2 with respect to the oxygen sensor element 1 is enhanced. The other features and effects are the same as those in the first embodiment.

(Third Embodiment)

A ceramic heater 2b in a third preferred embodiment is shown in FIGS. 6A, 6B. The ceramic heater 2b is composed of the heater substrate 201 holding heater layers 25 on both surfaces thereof, and two cover substrates 202 sandwiching the heater substrate 201 as shown in FIG. 6B. The front end portion 209b of the ceramic heater 2b is chamfered at four sides and at four corners thereof as shown in FIG. 6A. The ceramic heater 2b contacts the bottom portion 109 of the air chamber 100 at sixteen points of the front end portion 209b. Therefore, the ceramic heater 2b can quickly heat the oxygen sensor element 1. In addition, because the four sides and the four corners of the front end portion 209b are chamfered, its effect on the solid electrolyte body 10 of the oxygen sensor element 1 is minimized. The other features and effects are the same as those in the first embodiment.

(Fourth Embodiment)

A ceramic heater 2c in a fourth preferred embodiment has a barrel-like shape in cross section as shown in FIG. 7. The ceramic heater 2c is composed of the heater substrate 201 holding heater layers 25 on both surfaces thereof, and two cover substrates 202 sandwiching the heater substrate 201 as in the third embodiment. Each of the cover substrates 202 is made of a plate having a curved surface for serving as an outer side surface of the ceramic heater 2c. The ceramic heater 2c does no have an angular portion in cross section, thereby minimizing its effect on the solid electrolyte body 10. The front end portion of the ceramic heater 2c can be chamfered as in the third embodiment. The other features and effects are the same as those in the first embodiment.

(Fifth Embodiment)

Figure 8:
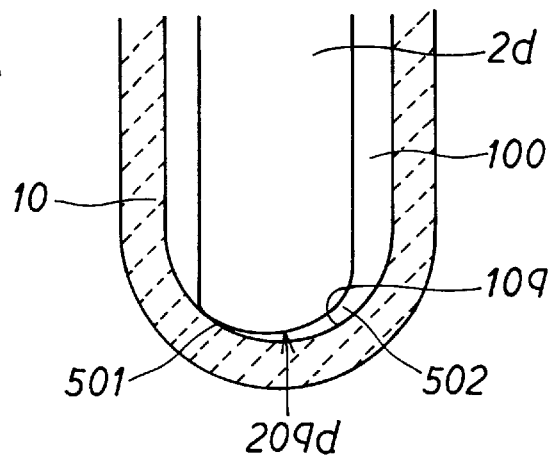
FIG. 8 is a cross-sectional view showing a front end portion of a ceramic heater installed within an air chamber of the oxygen sensor element in a fifth embodiment.

A ceramic heater 2d in a fifth preferred embodiment has a front end portion 209d with a front end curved face which is composed of two portions 501, 502. The portions 501, 502 have different radiuses of curvature from one another. FIG. 8 shows the ceramic heater 2d which is installed within the air chamber 100 of the oxygen sensor element 1. The portion 501 has a radius of curvature smaller than that of the bottom portion 109 of the air chamber 100, while the portion 502 has a radius of curvature larger than that of the portion 501.

In this case, even if the front end portion 209d of the ceramic heater 2d is sized incorrectly, the front end portion 209d of the ceramic heater 2d contacts the bottom portion 109 of the air chamber 100 at the portion 501. The mechanical strength of a typical ceramic heater is generally not so great that it cannot be inserted into the air chamber 100 with large force until the front end portion of the ceramic heater abuts the bottom portion 109 of the air chamber 100. The ceramic heater 2d can solve this problem.

In addition, even if the axis of the ceramic heater 2d deviates from the axis of the air chamber 100, the ceramic heater 2d contacts the bottom portion 109 of the air chamber 100 at the portion 501. The other features and effects are the same as those in the first embodiment.

(Sixth Embodiment)

Figure 9A:
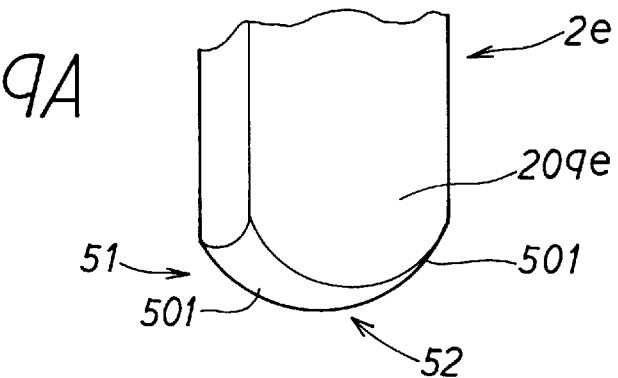
FIG. 9A is a perspective view showing a front end portion of a ceramic heater in a sixth embodiment.
Figure 9B:
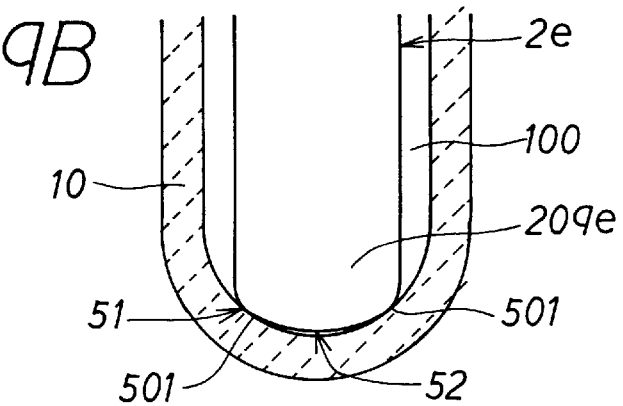
FIG. 9B is a cross-sectional view showing the front end portion of the ceramic heater installed within the air chamber of the oxygen sensor element in the sixth embodiment.

As shown in FIG. 9A, a ceramic heater 2e in a sixth preferred embodiment has a front end portion 209e with a front end curved face. The front end curved face is composed of a first front end face (tapered face) 51 and a second front end face (top face) 52 which is provided at the top portion of the front end curved face. The first front end face has a portion 501 with a radius of curvature that is smaller than that of the bottom portion 109 of the air chamber 100. Therefore, the ceramic heater 2e contacts the bottom portion 109 of the air chamber 100 at the portion 501 of the first front end face 51 as shown in FIG. 9B. The other features and effects are the same as those in the fifth embodiment.

(Seventh Embodiment)

Figure 10:
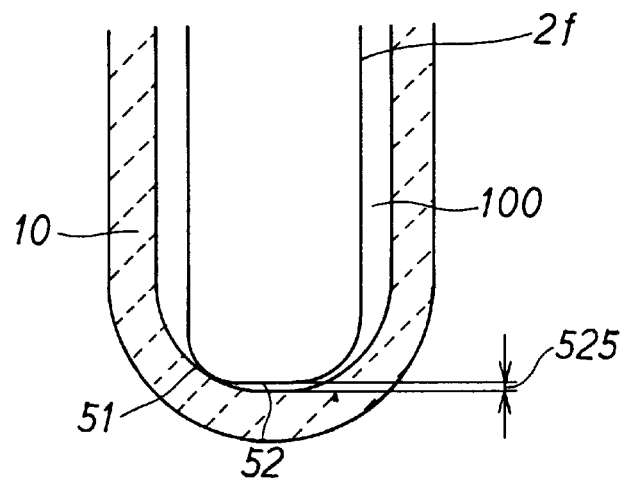
FIG. 10 is a cross-sectional view showing a front end portion of a ceramic heater installed within the air chamber of the oxygen sensor element in a seventh embodiment.

As shown in FIG. 10, a front end portion of a ceramic heater 2f in a seventh preferred embodiment has a first front end curved face 51 and a second front end curved face 52 which is provided at the top portion of the front end portion. The radius of curvature of the second front end curved face 52 is substantially equal to or larger than that of the bottom portion 109 of the air chamber 100. In this case, a clearance 525 between the bottom portion 109 and the second front end curved face 52 can be reduced. Therefore, even if the front end portion of the ceramic heater 2f does not entirely contact the bottom portion 109 of the air chamber, heat-transfer efficiency from the ceramic heater 2f to the oxygen sensor element 1 can be sufficiently increased. The other features and effects are the same as those in the fifth embodiment.

(Eighth Embodiment)

Figure 11A:
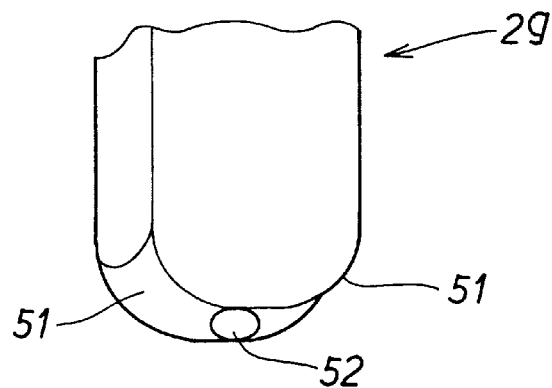
FIG. 11A is a perspective view showing a front end portion of a ceramic heater in an eighth embodiment.
Figure 11B:
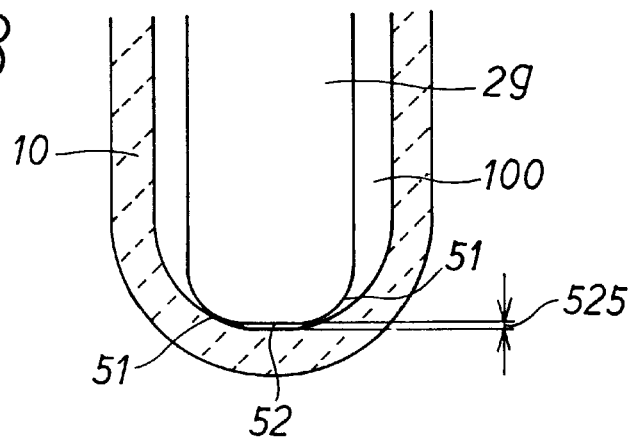
FIG. 11B is a cross-sectional view showing the front end portion of the ceramic heater installed within the air chamber of the oxygen sensor element in the eighth embodiment.

In an eighth preferred embodiment, as shown in FIGS. 11A, 11B, a front end portion of a ceramic heater 2g has a first front end curved face 51 and a second front end flat face 52, which is provided at the top portion of the front end portion.

The front end portion of the ceramic heater 2g is shaped only by forming the first front end curved face 51 by a polishing method or the like. The second front end flat face 52 can be provided without being processed. In a case where both of the first and second front end faces 51, 52 are formed by polishing or the like, there is a possibility that the heater or lead layer is exposed from the front end portion. As opposed to this, in the eighth embodiment, because the second front end flat face 52 need not be polished, the front end portion is prevented from being excessively polished. Therefore, the heater layer and the lead layer are not exposed by forming the front end portion.

It is apparent that the clearance 525 between the bottom portion 109 of the air chamber 100 and the front end portion of the ceramic heater 2g can be reduced to provide sufficient heat transfer as in the seventh embodiment. The other features and effects are the same as those in the fifth embodiment.

Figure 12A:
FIG. 12A is a schematic plan view showing a bottom face of the front end portion of the ceramic heater of the seventh or eighth embodiment.
Figure 12B:
FIGS. 12B, 12C are schematic views showing contact portions between the front end portion of the oxygen sensor element and the ceramic heater of the seventh or eighth embodiment.
Figure 12C:
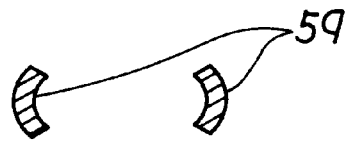

In the ceramic heater 2f or 2g of the seventh or eighth embodiment, the bottom face of the front end portion, which is composed of the first and second front end faces 51, 52, is shown in FIG. 12A. The ceramic heater 2f or 2g can contact the bottom portion 109 of the air chamber 100 at two lines as shown in FIG. 12B or at two faces as shown in FIG. 12C. In FIGS. 12B, 12C, reference numerals 58, 59 indicate contact portions between the ceramic heater 2f or 2g and the bottom portion 109 of the air chamber 100.

(Ninth Embodiment)

Figure 13:
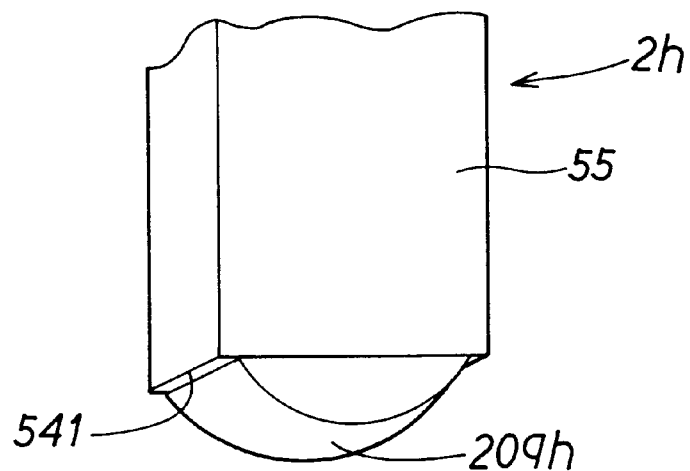
FIG. 13 is a perspective view showing a front end portion of a ceramic heater in a ninth embodiment.

A ceramic heater 2h in a ninth preferred embodiment has a body 55 and a front end portion 209h with a front end curved face as shown in FIG. 13. The front end portion 209h is integrally connected to the body 55 via a step portion 541. Accordingly, the ceramic heater 2h certainly contacts the bottom portion 109 of the air chamber 100 at the front end portion 209h thereof. The other effects are the same as those in the above-mentioned embodiments.

(Tenth Embodiment)

In a tenth preferred embodiment, a relationship between shapes of front end portions of ceramic heaters and activation times of the ceramic heaters will be described. That is, in the tenth embodiment, five ceramic heaters with front end portions having various kinds of shapes were respectively installed in oxygen sensor elements, and those activation times were measured. The activation time of each of the oxygen sensor elements is the time required for the integrated ceramic heater to raise the temperature of an outside front end of the oxygen sensor element to 300° C. after the heater element is energized.

The ceramic heaters employed in the tenth embodiment will be specifically described as comparative sample C1 and as samples 1–4, with reference to FIGS. 14A–18B. FIGS. 14A, 15A, 16A, 17A, 18A show the front end portions of the ceramic heaters, while FIGS. 14B, 15B, 16B, 17B, 18B show the front end faces of the ceramic heaters. In FIGS. 15B, 16B, white circles represent contact points where the front end portion and the bottom face 109 of the air chamber 100 contact one another.

Figure 14A:
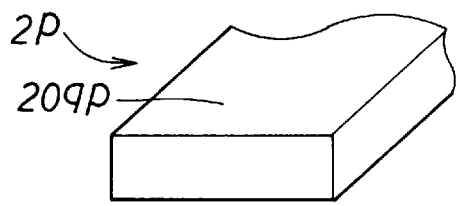
FIGS. 14A, 14B are perspective and cross-sectional views showing comparative sample C1 in a tenth embodiment.
Figure 14B:
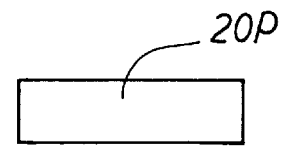

Comparative sample C1 shown in FIGS. 14A, 14B is a conventional ceramic heater 2p. The front end portion 209p of the ceramic heater 2p has a rectangular parallelopiped shape with a rectangular front end face 20p. The front end face 20p does not contact the bottom portion 109 of the air chamber 100.

Figure 15A:
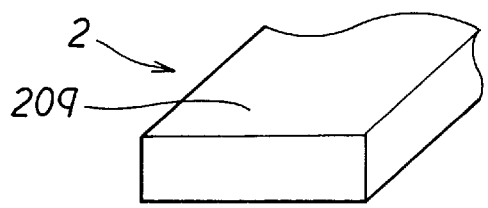
FIGS. 15A, 15B are perspective and cross-sectional views showing sample 1 in the tenth embodiment.
Figure 15B:
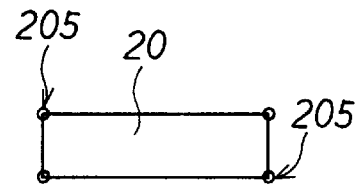

Sample 1 shown in FIGS. 15A, 15B is the ceramic heater 2 in the first embodiment. The front end portion 209 of the ceramic heater 2 is a rectangular paralleopiped shape with the rectangular front end face 20. The front end face 20 contacts the bottom portion 109 of the air chamber 100 at the corners thereof.

Figure 16A:
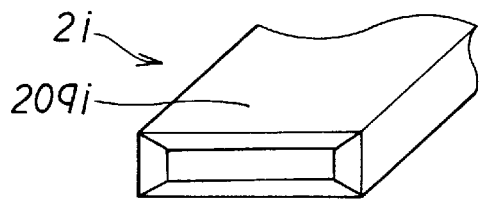
FIGS. 16A, 16B are perspective and cross-sectional views showing sample 2 in the tenth embodiment.
Figure 16B:
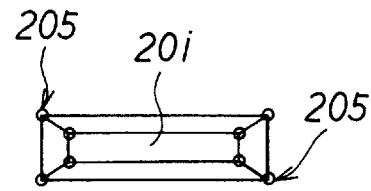

Sample 2 shown in FIGS. 16A, 16B is a ceramic heater 2i having a front end portion 209i chamfered (tapered) at four portions. The chamfered front end portion 209i has a rectangular front end face (top face) 20i smaller than the base portion thereof, and contacts the bottom portion 109 of the air chamber 100 at eight points. The ceramic heater 2i is a modified one of the ceramic heater 2b in the third embodiment (see FIGS. 6A, 6B).

Figure 17A:
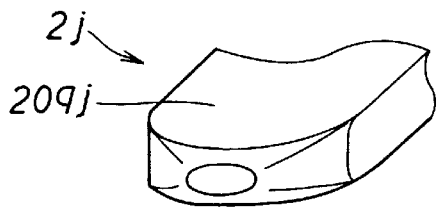
FIGS. 17A, 17B are perspective and cross-sectional views showing sample 3 in the tenth embodiment.
Figure 17B:
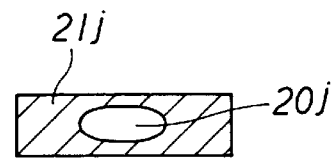
Figure 18A:
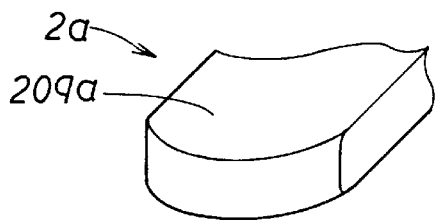
FIGS. 18A, 18B are perspective and cross-sectional views showing sample 4 in the tenth embodiment.
Figure 18B:

Sample 3 shown in FIGS. 17A, 18B is a ceramic heater 2j having a tapered front end portion 209j. The tapered front end portion 209j has an ellipse-like front end flat face 20j on the top portion thereof and a tapered and curved front end face 21j around the front end flat face 20j. The tapered and curved front end face 21j is formed to entirely contact the bottom portion 109 of the air chamber 100. In FIG. 17B, the contact portion is indicated with slat lines. The ceramic heater 2j is a modified one of the ceramic heater 2f or 2g of the seventh or eighth embodiment (see FIGS. 10, 11A, 11B).

Sample 4 shown in FIGS. 18A, 18B is the ceramic heater 2a in the second embodiment. The front end portion 209a of the ceramic heater 2a has the front end curved face 20a with the same radius of curvature as that of the bottom portion 109 of the air chamber 100. The curved surface contacts the entire bottom portion 109 of the air chamber. In FIG. 10B, the contact portion is indicated with slant lines as well.

Figure 19:
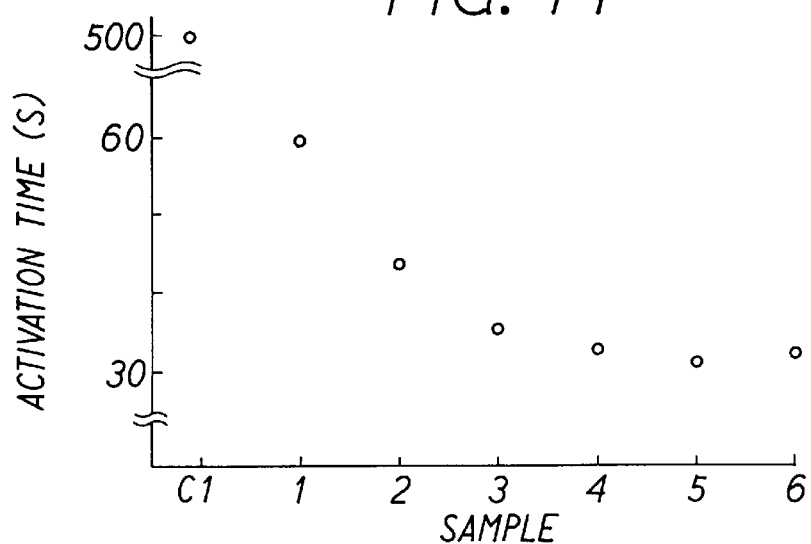
FIG. 19 is a graph showing activation times of samples C1, and 1–6.

FIG. 19 shows the activation times of the oxygen sensor elements respectively holding comparative sample C1 and samples 1–4. FIG. 19 further shows activation times of samples 5, 6, which are the ceramic heaters 2g of the eighth embodiment having diameters of the second front end flat faces 52 different from one another (see FIGS. 11A, 11B). Specifically, sample 5 has the second front end face 52 with a diameter of 0.5 mm, and sample 6 has the second front end face 52 with a diameter of 1.0 mm.

As understood from FIG. 19, the activation time of comparative example C1 is the longest of all. Further, it is confirmed that the larger the contact area between the front end portion of the ceramic heater and the bottom portion 109 of the oxygen sensor element 1, the shorter the activation time becomes. In FIG. 19, despite the contact area of sample 4 being larger than that of sample 5, the activation time of sample 4 is slightly longer than that of sample 5. Concerning this point, it is assumed that sample 4 had a processing error and thereby did not have the same radius of curvature as that of the bottom portion 109 of the air chamber, so that the contact area of sample 4 was slightly smaller than that of sample 5.

When the oxygen sensor element whose activation time is sufficiently short is installed in an exhaust system of an internal combustion engine, the oxygen sensor element can precisely detect an oxygen concentration or the air fuel ratio of an exhaust gas immediately after the engine starts.

Figure 20:
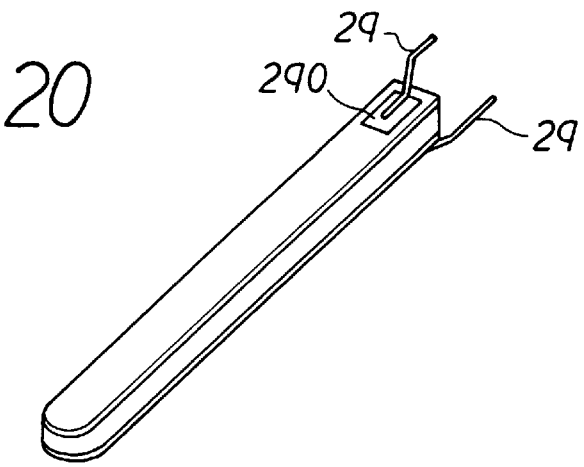
FIG. 20 is a perspective view showing a modified ceramic heater of the present invention.
Figure 21A:
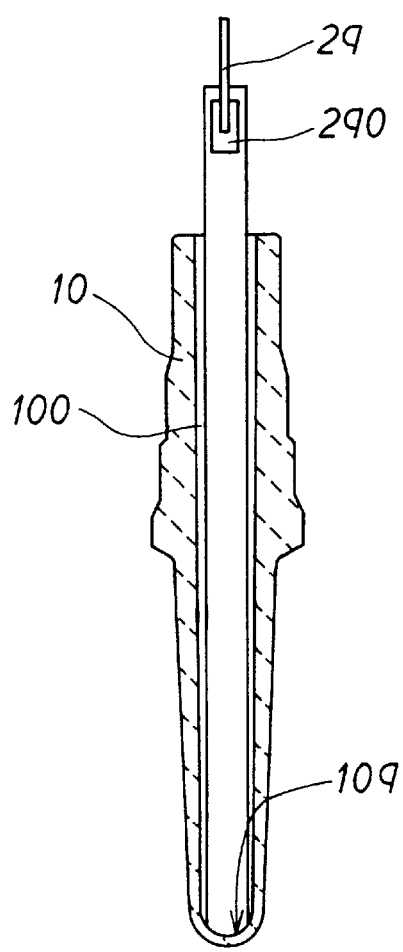
FIGS. 21A, 21B are cross-sectional views showing the modified ceramic heater of FIG. 20 that is installed in the oxygen sensor element.
Figure 21B:
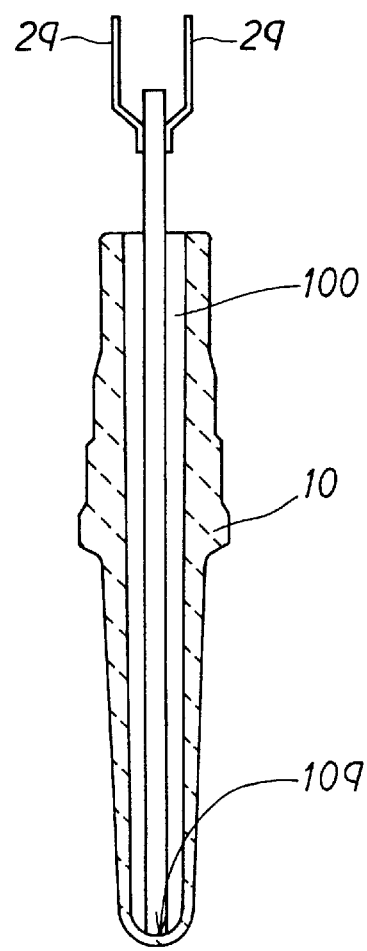

Further, the present invention can be applied to a ceramic heater shown in FIG. 20. That is, the lead wires 29 can be bonded to main surfaces of the ceramic heater via the conductive members 290. FIGS. 21A, 21B show a state where the ceramic heater of FIG. 20 is installed in the solid electrolyte body 10 of the oxygen sensor element 1. The other features are the same as those of the above-mentioned embodiments, and therefore it is apparent that the ceramic heater of FIG. 20 have the same effects as those of the above mentioned embodiments.

While the present invention has been shown and described with reference to the foregoing preferred embodiment, it will be apparent to those skilled in the art that changes in form and detail may be made therein without departing from the scope of the invention as defined in the appended claims.

What is claimed is:

1. An oxygen sensor element comprising:
   a solid electrolyte body defining an air chamber therein;
   an outer electrode disposed on an outer surface of the electrolyte body;
   an inner electrode disposed on an inner surface of the electrolyte body to be exposed to the air chamber; and
   a plate-like lamination type ceramic heater disposed within the air chamber and having an end portion contacting the inner surface of the electrolyte body at a bottom portion of the air chamber.

2. The oxygen sensor element of claim 1, wherein the end portion of the ceramic heater contacts the inner surface of the electrolyte body at a plurality of contact points.

3. The oxygen sensor element of claim 1, wherein the end portion of the ceramic heater is tapered.

4. The oxygen sensor element of claim 1, wherein the end portion of the ceramic heater has a curved face with a radius of curvature substantially the same as that of the bottom portion of the air chamber.

5. The oxygen sensor element of claim 1, wherein the end portion of the ceramic heater has a line and the inner surface of the electrolyte body contacts the entire line of the end portion of the ceramic heater.

6. The oxygen sensor element of claim 1, wherein the end portion of the ceramic heater has a face and the inner surface of the electrolyte body contacts the entire face of the end portion of the ceramic heater.

7. The oxygen sensor element of claim 1, wherein the end portion of the ceramic heater has a curved face with a radius of curvature smaller than that of the bottom portion of the air chamber.

8. The oxygen sensor element of claim 7, wherein the end portion of the ceramic heater has first and second end faces each having a different radius of curvature.

9. The oxygen sensor element of claim 8, wherein:
   the first end face is the curved face having the radius of curvature smaller that of the bottom portion of the air chamber, and is disposed farther from a top portion of the end portion than the second end face.

10. The oxygen sensor element of claim 1, wherein the end portion of the ceramic heater has a first end face and a second end face disposed closer to a top portion of the end portion than the first end face and having a radius of curvature larger than that of the bottom portion of the air chamber.

11. The oxygen sensor element of claim 10, wherein the first end face has a radius of curvature smaller than that of the bottom portion of the air chamber.

12. The oxygen sensor element of claim 10, wherein the second end face is flat.

13. An oxygen sensor element comprising:
   a solid electrolyte body defining an air chamber therein;
   an outer electrode disposed on an outer surface of the electrolyte body;
   an inner electrode disposed on an inner surface of the electrolyte body within the air chamber; and
   a plate-like lamination type ceramic heater disposed within the air chamber and having an end portion contacting the inner surface of the electrolyte body at a bottom portion of the air chamber, the end portion including two faces each with a different radius of curvature.

14. The oxygen sensor element of claim 13, wherein the end portion is tapered to have a tapered face contacting the inner surface of the electrolyte body and a top face provided on a top portion of the end portion.

15. The oxygen sensor element of claim 14, wherein the top face is flat.

16. The oxygen sensor element of claim 15, wherein the plate-like lamination type ceramic heater is manufactured by steps of;
   preparing a plate-like lamination body; and
   tapering an end portion of the plate-like lamination body to remain a top flat face.

17. The oxygen sensor element of claim 14, wherein the tapered face entirely contacts the inner surface of the electrolyte body.

18. The oxygen sensor element of claim 14, wherein the top face has a radius of curvature larger than that of the bottom portion of the air chamber and the tapered face has portion with a radius of curvature smaller than that of the bottom portion of the air chamber.

* * * * *